United States Patent
Hedrick et al.

(10) Patent No.: US 10,881,682 B2
(45) Date of Patent: Jan. 5, 2021

(54) THERAPEUTIC COMPOSITIONS COMPRISING N-ALKYL-HYDROXY POLYMERS

(71) Applicant: INTERNATIONAL BUSINESS MACHINES CORPORATION, Armonk, NY (US)

(72) Inventors: James Hedrick, San Jose, CA (US); Dylan Boday, San Jose, CA (US); Jeannette Garcia, San Jose, CA (US); Rudy Wojtecki, San Jose, CA (US); Yi Yan Yang, The Nanos (SG); Chuan Yang, The Nanos (SG)

(73) Assignee: International Business Machines Corporation, Armonk, NY (US)

( * ) Notice: Subject to any disclaimer, the term of this patent is extended or adjusted under 35 U.S.C. 154(b) by 127 days.

(21) Appl. No.: 14/836,614

(22) Filed: Aug. 26, 2015

(65) Prior Publication Data
US 2017/0056513 A1    Mar. 2, 2017

(51) Int. Cl.
*A61K 31/7088* (2006.01)
*A61K 47/59* (2017.01)
*C12N 15/87* (2006.01)

(52) U.S. Cl.
CPC .......... *A61K 31/7088* (2013.01); *A61K 47/59* (2017.08); *C12N 15/87* (2013.01)

(58) Field of Classification Search
CPC ............ A61K 47/48192; A61K 31/713; A61K 48/00; A61K 31/7088; C12N 15/87
See application file for complete search history.

(56) References Cited

U.S. PATENT DOCUMENTS 3,786,113 A * 1/1974 Vassileff ............... C08L 33/062
525/113
8,507,270 B2    8/2013 Yamaguchi et al.

2010/0331234 A1 * 12/2010 Mahon ................. A61K 9/1271
514/1.1
2011/0020927 A1    1/2011 Yamaguchi et al.
2013/0292606 A1    11/2013 Yamaguchi et al.

FOREIGN PATENT DOCUMENTS

| CN | 102703486 A | 10/2012 |
|---|---|---|
| CN | 103588998 A | 2/2014 |
| CN | 103642840 A | 3/2014 |
| JP | 2011024493 A | 2/2011 |
| KR | 1020060025711 | 3/2006 |
| KR | 1020100038686 | 4/2010 |
| KR | 1020120088215 | 8/2012 |

OTHER PUBLICATIONS

Tripathi Synth.N-(2,3-dihydroxypropyl)-PEIs , Mol.BioSyst. 2012, p. 1426.*
Gibney Poly(ethylene imine)s Macromolecular Bioscience, p. 1279 (Year: 2012).*
Park et al. "Degradable Polyethylenimine-alt-poly (ethylene glycol) Copolymers as Novel Gene Carriers", Science Direct. Journal of Controlled Release, 2005. pp. 367-380.
Kim et al. "Polyethylenimine with Acid-Labile Linkages as a Biodegradable Gene Carrier", Science Direct, Journal of Controlled Release, 2005. pp. 209-219.
Arote et al. "A Biodegradable Poly(ester amine) Based on Polycaprolactone and Polyethylenimine as a gene Carrier", Science Direct. Biomaterials, 2007. pp. 735-744.
Forrest et al. "A Degradable Polyethylenimine Derivative with Low Toxicity for Highly Efficient Gene Delivery Bioconjugate Chem.", 2003, 14 (5), pp. 934-940.

* cited by examiner

*Primary Examiner* — Matthew P Coughlin
*Assistant Examiner* — Thurman Wheeler
(74) *Attorney, Agent, or Firm* — Patterson + Sheridan, LLP

(57) ABSTRACT

The disclosure describes methods and therapeutic compositions comprising polymers modified with N-alkyl-hydroxy groups comprising one or more carbon atoms. The compositions are useful for gene delivery, and exhibit broad-spectrum antiviral activity and low toxicity in vitro.

Figure 1A:
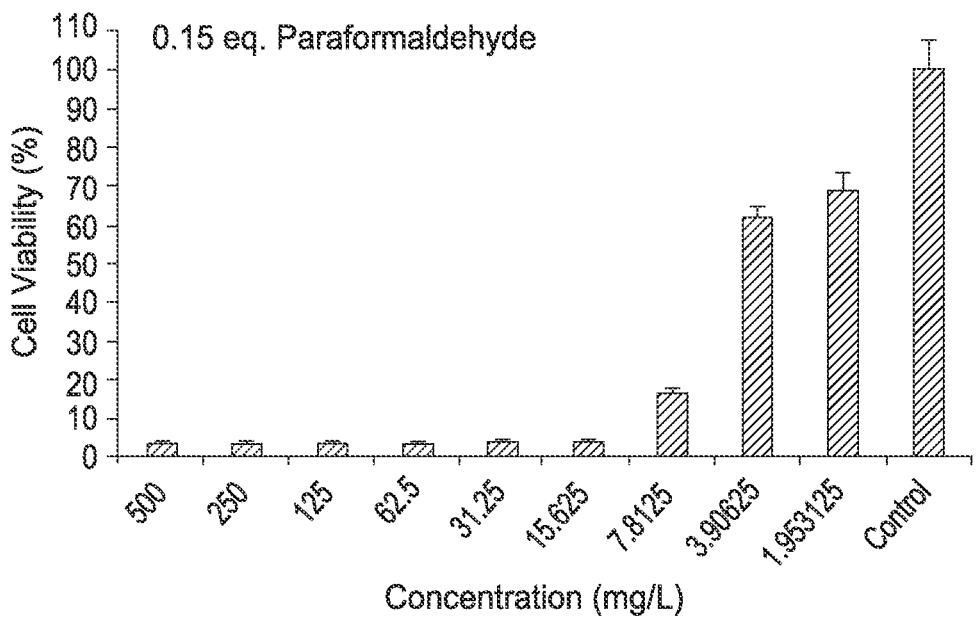
Figure 1B:
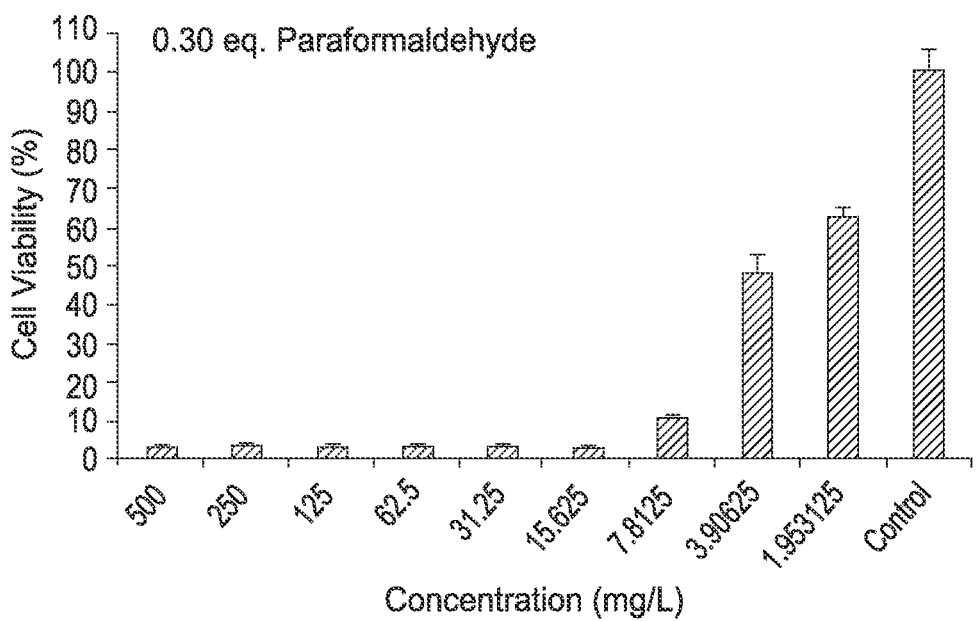
Figure 1C:
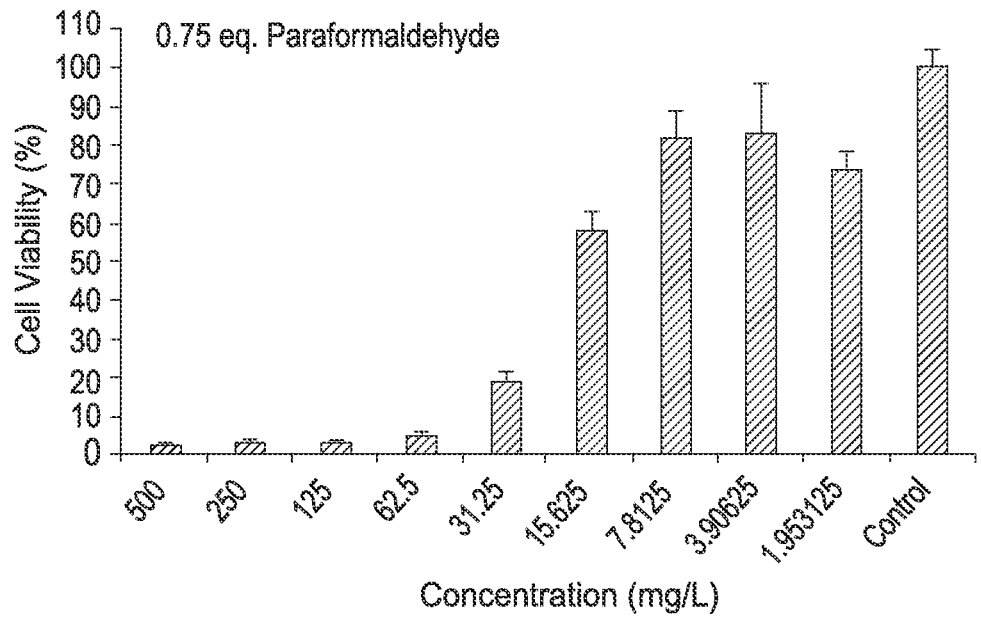

14 Claims, 2 Drawing Sheets and figures illustrate only typical embodiments of the disclosure
THERAPEUTIC COMPOSITIONS COMPRISING N-ALKYL-HYDROXY POLYMERS

FIELD

The disclosure relates to methods and therapeutic compositions comprising polymers modified with N-alkyl-hydroxy groups. The compositions are useful for gene delivery, and exhibit broad-spectrum antiviral activity and low toxicity in vitro.

BACKGROUND

Nucleic acid-based therapies involving gene transference hold great promise in the treatment of human diseases. In principle, faulty and defective genes may be corrected and replaced by functional ones, but redundant gene expression may also be repressed to a normal level by the use of RNA interference. There are two major gene delivery vectors, viral and non-viral. Viral vectors have superior transduction capabilities, but the immunogenic and oncogenic potentials of viral vectors have limited their clinical applications. To solve this problem, non-viral gene delivery systems have been developed, and feature number of advantages including improved biosafety, lower production costs, ease of transportation and storage, and reproducibility. Despite these advantages, non-viral systems have thus required specific molecular tailoring for specific interaction with certain nucleic acids and cell surfaces. To improve on the state of the art, there is a need for new non-viral gene delivery systems that display high therapeutic activity, low toxicity and exhibit broad recognition for the myriad of nucleic acids and cell surfaces found in nature.

Many of the desirable characteristics that are sought after in non-viral gene delivery systems have utility and application in the field of antiviral therapeutics. In recent years, viral infections have emerged as the preeminent global public health problem because of an increasing human population, aging, global warming, and medical treatments that suppress the immune system, including irradiation therapy, anti-cancer chemotherapy and organ transplantation. Effective treatment of viral infections is elusive because of the variance in virus structure (enveloped and non-enveloped viruses) together with their ability to rapidly mutate and garner resistance.

To solve the aforementioned problems found with the current materials and compositions in these fields, new therapeutic compositions that display efficacy in both gene delivery and in antiviral applications have been developed, and are the subject of the present disclosure. The new compositions involve N-alkyl-hydroxy modified polymers, which exhibit: a) high gene transfection efficiency in vitro, b) display broad-spectrum antiviral activity, c) remain active despite viral mutation(s), d) exhibit high virus selectivity, e) display low toxicity in vitro; and f), are biodegradable.

SUMMARY

A therapeutic composition is described having at least one polymer comprising amine end groups, secondary amine groups, tertiary amine groups, and alkyl-hydroxy groups, wherein at least 5% of the secondary and tertiary amine groups comprise N-alkyl-hydroxy groups, and wherein at least 5% of the amine end groups comprise N-alkyl-hydroxy groups.

A method for producing a therapeutic composition is also described that includes forming a reaction mixture comprising a solvent, a polymeric amine and a N-alkyl-hydroxy group precursor; and heating the mixture at a temperature from about 25° C. to about 150° C. to produce a polymer comprising secondary and tertiary amine groups, wherein at least 5% of the secondary and tertiary amine groups are N-alkyl-hydroxy groups.

BRIEF DESCRIPTION OF THE DRAWINGS AND FIGURES

So that the manner in which the above recited features of the present disclosure can be understood in detail, a more particular description of the disclosure, briefly summarized above, may be had by reference to embodiments, some of which are illustrated in the appended drawings and figures. It is to be noted, however, that the appended drawings and figures illustrate only typical embodiments of the disclosure and are therefore not to be considered limiting of its scope, for the disclosure may admit to other equally effective embodiments.

FIGS. 1A-1D are charts representing data collected according to some embodiments of the disclosure.

DETAILED DESCRIPTION

The present disclosure describes new therapeutic compositions that are useful for gene delivery, prevention of viral infection, and are transparent to viral mutation, thus mitigating resistance development. The mode of action of the new therapeutic compositions comprising N-alkyl-hydroxy substituted polymers is related to non-specific supramolecular interactions, such as hydrogen-bonding and electrostatic interactions, between the functional groups of the therapeutic composition polymer(s) and biological compounds such as nucleic acids, genes, proteins, RNA, DNA and virus/cell surfaces. The polymers of the therapeutic composition may have N-alkyl-hydroxy groups, secondary and tertiary amine groups, and charged groups (cationic groups), such as quaternary amine groups at biological pH. For the purposes of the disclosure, binding generally refers to chemical interactions including but not restricted to: chemical bonding, covalent bonding, hydrogen bonding, polar attraction, and dissimilar charge attraction such as positive and negative charge attraction.

In some embodiments, an N-alkyl-hydroxy substituted polymer of the therapeutic composition may form a complex with nucleic acids such as therapeutic DNA and/or RNA, and the complex may be further internalized into cells. Upon and after cell uptake, the N-alkyl-hydroxy groups and the secondary and tertiary amine groups of the nucleic acid/polymer complex may aid, deliver or otherwise enable the release of the nucleic acid from the complex. In other embodiments, the therapeutic composition may form polymer-virus and polymer-cell assemblies based on the aforementioned interactions. The formation of said assemblies is not affected, negatively impacted, nor dependent on viral mutation, thus preventing viral resistance to the therapy. For example, the polymer N-alkyl hydroxy groups of polymer-virus and polymer-cell assemblies may further neutralize endosomal pH (absorb or bind H') thus creating an inhospitable environment for viral replication and further viral infection.

The aforementioned therapeutic activity may be realized when at least 5% of the amine groups of the composition are substituted with N-alkyl hydroxy groups, which have at least one carbon atom. The polymers of the therapeutic composition may further include a plurality of polymer chain amine end groups (terminal groups) and/or pendant amine end groups, wherein at least 5% of the groups may be substituted with at least one N-alkyl hydroxy group comprising at least one carbon atom. The 5% substitution produces a therapeutic composition that generally comprises a plurality of secondary and tertiary amine groups with N-alkyl-hydroxy group substitution, and secondary and tertiary amine groups that may be unsubstituted. In some embodiments, all of the amine groups of the polymeric composition may have N-alkyl-hydroxy groups.

In some embodiments of the disclosure, the N-alkyl-hydroxy modification of primary and/or secondary amine groups may decrease or eliminate cell toxicity, and may temper or mediate the buffering capacity of the therapeutic composition. For example, the basic nature and nucleophilic character of a primary amine may be decreased or modified by the addition of groups such as N-alkyl-hydroxy groups. Significantly, the percent substitution of N-alkyl-hydroxy groups, the number of carbon atoms contained in the N-alkyl-hydroxy groups, and the resultant molecular and supramolecular conformations provide structural flexibility and enhanced bonding interactions with nucleic acids such as DNA, RNA and/or a virus surface. More specifically, the N-alkyl-hydroxy substituted polymer may uniquely bind, bond, adhere, conform, flex, and wrap over, upon, and/or around the unique structural features that are found in the myriad of nucleic acids and virus surfaces, such as primary, secondary, tertiary, and quaternary structures, and thus may form a complex with a nucleic acid such as DNA or RNA, and/or bind to a virus/cell surface and otherwise render a virus biologically inactive.

As mentioned prior, the bonding interactions may be hydrogen bonding and/or electrostatic interactions involving positive and negative charges. For example, polymers comprising amine groups may have high cationic (positive) charge density at physiological pH, wherein about 50% to about 90% of the amine groups have a positive charge due to the binding of a proton ($H^+$). Specifically, and in combination with the hydrogen bonding interactions, the positively charged amine groups may engage in electrostatic interactions with negatively charged nucleic acids, nucleic acid residues, and/or proteins over a broad pH range. The combination of hydrogen bonding and electrostatic interactions may generally result in the strong bonding of therapeutic N-alkyl-hydroxy polymers to nucleic acids and virus/cell surfaces.

In one embodiment, the therapeutic composition may include more than one N-alkyl-hydroxy substituted polymer. For example, the composition may be a mixture of N-alkyl-hydroxy modified polymers with differing molar amounts of N-alkyl-hydroxy substitutions on the polymer chain. In another embodiment, the therapeutic composition may have at least one N-alkyl-hydroxy substituted polymer, which may be linear or branched, or a mixture of N-alkyl-hydroxy substituted polymers that may be linear or branched. N-alkyl-hydroxy substitution may be found at amine groups integrated in the polymer chain backbone or repeating units, amine groups located at polymer chain ends, or at sites where the amine groups may be pendant end groups or are a part of a pendant group or a branch. For the purposes of this disclosure amine groups not integrated in the polymer backbone may be thought of as amine end groups. Polymers of the composition may be at least 500 grams/mole in molecular weight (number average) as measured by techniques such as is gel permeation chromatography (GPC), also known as size exclusion chromatography (SEC). Examples of polymers of the therapeutic composition amenable to N-alkyl-hydroxy substitution by contact with electrophilic N-alkyl-hydroxy precursors may be selected from the group consisting of polyethylenimine, polyvinylamine, polyallylamine, polyamino acrylates, polyamino methacrylates, copolymers, and salts thereof. Electrophilic N-alkyl-hydroxy precursors suitable for nucleophilic substitution upon exposure to the aforementioned polymers, and comprising at least one carbon atom, may be selected from the group consisting of: formaldehyde, aqueous formaldehyde, formalin, 1,3,5-trioxane, metaformaldehyde, paraformaldehyde, glyoxylic acid, MP-glyoxylate, hexamethylenetramine, dimethoxymethane, formyl cation equivalent, and a mixture comprising dimethyl sulfoxide and a strong acid. The aforementioned group of compounds may produce a one carbon N-alkyl-hydroxy group (carbon attached to a polymer nitrogen atom) that is referred to as a hemiaminal group.

As illustrated in reaction example 1, an N-alkyl-hydroxy/hemiaminal substituted polymer of the therapeutic composition may be produced by the reaction of polyethylenimine (PEI) and paraformaldehyde ($(CH_2O)_n$) in dimethyl sulfoxide (DMSO) solvent over a time period from about 0.5 hour to about 2 hours:

REACTION EXAMPLE 1

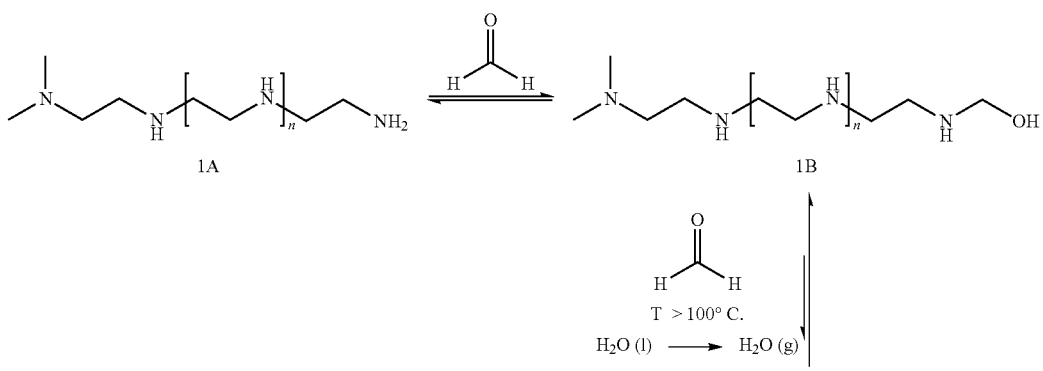

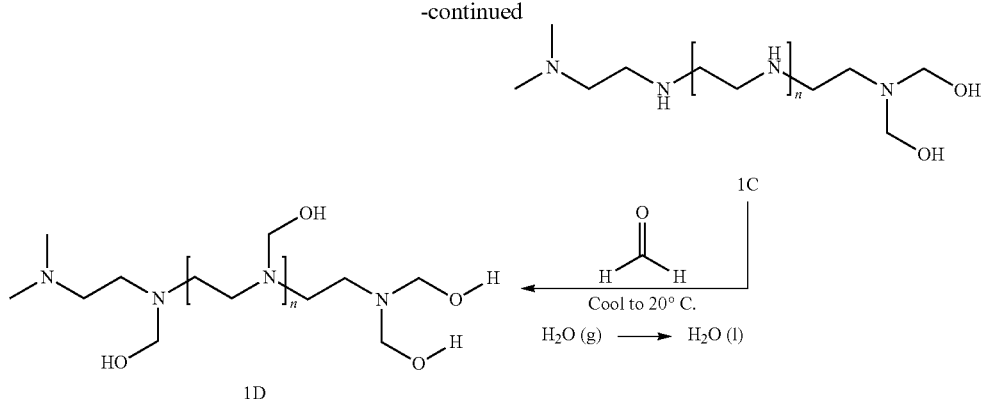

Reaction example 1 illustrates the step-wise formation of N-alkyl-hydroxy/hemiaminal substituted polymers (1B-1D) based on PEI (1A). In the scheme, 1A is contacted with formaldehyde, or a suitable precursor, to produce N-alkyl-hydroxy/hemiaminal polymer 1B (with chain end group mono-substitution) at a temperature of at least 100° C., to drive off water by-product, and thus drive the equilibrium to the 1B product side of the equation. Further equivalents of formaldehyde produce 1C, with bis-N-alkyl-hydroxy/bis-hemiaminal end group substitution. Finally, 1D represents a fully substituted N-alkyl-hydroxy/hemiaminal polymer comprising tertiary amine groups isolated upon cooling. Reaction example 1 does not restrict the number, combination, or type of N-alkyl-hydroxy substitution. For example, the composition may include polymer chains with completely substituted amine groups, while other polymer chains may be partially substituted. It is further noted that embodiments of the disclosure do not restrict the use of a mixture, or mixtures comprising amine polymers to produce N-alkyl-hydroxy modified polymers. Additionally, the practitioner may utilize any copolymer comprising amine groups, such as polyethylenimine-graft-poly(ethylene glycol) (PEI-g-PEG) for example. In some embodiments, linear or branched PEI, or a mixture thereof, may be contacted with paraformaldehyde to generate the requisite N-alkyl-hydroxy/hemiaminal polymer at a temperature of about 110° C., in the presence of triethylamine (TEA), and wherein the concentration of paraformaldehyde may range from about 0.15 to about 1.2 equivalents. The polymer product, as mixed or dissolved in the DMSO solvent, may be isolated by precipitation, wherein the polymer/DMSO solution is slowly added to a well stirred suitable precipitation solvent, such as acetone, followed by filtration, washing, and drying. Diffusion-ordered nuclear magnetic resonance spectroscopy (DOSY-NMR) and other 2D NMR techniques may be used to analyze the polymer product and identify the peaks corresponding to N-alkyl-hydroxy/hemiaminal moieties. In one example, 0.5 equivalents of paraformaldehyde generated a new peak which may be identified as a bis-hemiaminal moiety. A desired number average molecular weight of at least 500 g/mole may be measured by gel permeation chromatography or similar techniques.

In some embodiments, a small molecule organic base, such as a tertiary amine, for example TEA, is added to the reaction mixture, so that the effective concentration is from about 0.1 mole/L to about 1 mole/L to suppress the formation of polymer cross-links (due to hexahydrotriazine formation) and thus promote the formation of the bis-hemiaminal end groups. Absent such a cross-link suppressing agent, a cross-linked polymer may not form effective or strongly bound complexes with topologically complex nucleic acids or viral/cell surfaces, because the cross-linked polymer may have restricted freedom of movement as a result of the more rigid structure.

In brief summary, reaction example 1 is not meant to limit or restrict the compositions or methods embodied in this disclosure, but rather only serves to illustrate some possible N-alkyl-hydroxy therapeutic compositions that may be produced from such a process. Indeed, the degree of N-alkyl-hydroxy/hemiaminal substitution may be controlled and adjusted by the practitioner to produce a general therapeutic composition with the desired binding configurations and interactions with complex nucleic acids and virus/cell surfaces.

Figure 1D:
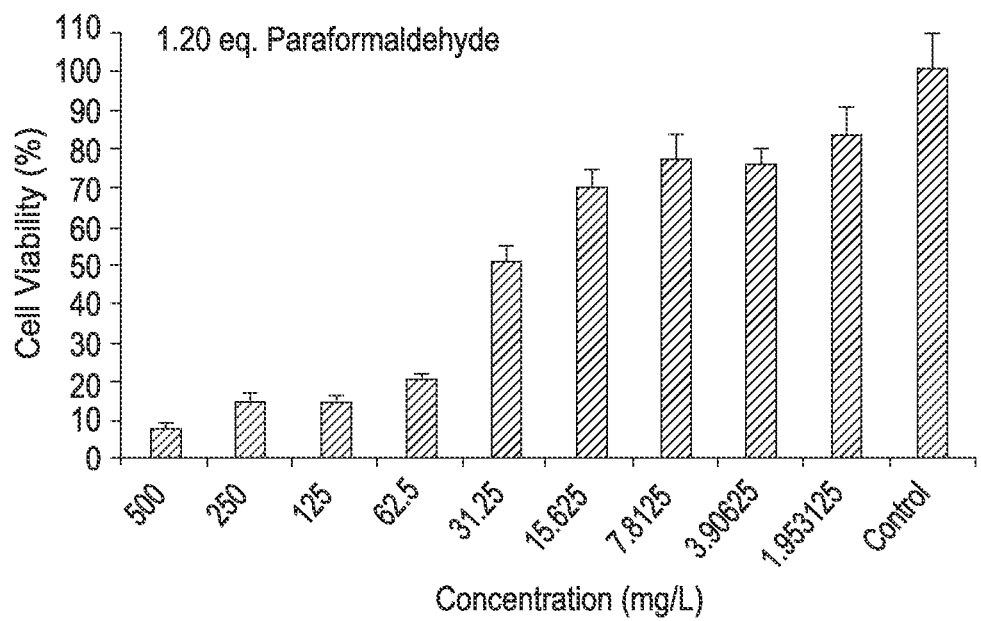

The toxicity profile of the therapeutic compositions of the disclosure may be adjusted by the N-alkyl-hydroxy/hemiaminal substitution. In some embodiments, therapeutic compositions comprising N-alkyl-hydroxy/hemiaminal modified polymers may exhibit significantly improved cell viability when exposed to N-alkyl-hydroxy/hemiaminal modified PEI in contrast to exposure to unmodified PEI. For example, in some experiments, viable human cells exposed to N-alkyl-hydroxy/hemiaminal modified PEI may display greatly decreased cell mortality in contrast to an unmodified PEI control. In further experiments, N-alkyl-hydroxy modified PEI with increasing molar amounts of N-alkyl-hydroxy/hemiaminal groups in the order: 0.15, 0.30, 0.75, and 1.2 equivalents were exposed to viable human embryonic kidney (HEK) 293 cells at differing concentrations, and MTT (tetrazolium dye) assays were performed. As shown in FIGS. 1A-1D, MTT assays confirm that cell viability/metabolic activity increases with increasing N-alkyl-hydroxy/hemiaminal group substitution, as the polymer dosing or concentration decreases to 1.95 mg/L. In one embodiment, as illustrated by FIG. 1D, the highest level of substitution (1.20 eq. of paraformaldehyde) renders N-alkyl-hydroxy/hemiaminal group modified PEI essentially non-toxic, at a concentration of 1.95 mg/L, and cell viability is comparable to a control with no polymer added to the mixture.

In other embodiments of the disclosure, N-alkyl-hydroxy compositions comprising N-alkyl-hydroxy groups that have two or more carbon atoms may be produced from epoxide precursors. In one embodiment, an epoxide, when contacted or reacted with the aforementioned polymers, may produce an epoxide adduct, or N-alkyl-hydroxy group, that may be an N-ethyl-hydroxy group. For example, when the epoxide is ethylene oxide or oxirane, an N-ethyl-hydroxy group may be produced, without further alkyl substitution or attached functionality, other than a hydrogen atom. In another example, PEI is contacted or reacted with 1,2-epoxydodecane, to introduce non-polar character to the polymer composition. Here, an N-ethyl-hydroxy group is formed, wherein the N-ethyl-hydroxy group has further substitution in the form of a —$CH_2(CH_2)_8CH_3$ chain attached to a hydroxyl carbon. Generally, when an epoxide is reacted with an amine polymer of the disclosure, an N-ethyl-hydroxy group is produced, with unrestricted further substitution possible at the hydroxyl carbon. There is no restriction in the type of epoxide used, nor on the number of carbon atoms or other atoms or functional groups that include the epoxide molecule. For example, the epoxide may be monomeric, oligomeric, polymeric and/or multifunctional.

In other embodiments of the disclosure, the composition may include at least one polymer wherein the N-alkyl-hydroxy substitutions are not restricted by the disclosure, and therefore the practitioner may choose any order of addition of such reagents to create the desired mixed polymer product. For example, the practitioner may choose to react glycidol with a polymer first, followed by the smaller and more reactive hemiaminal precursor, which has less steric requirements.

As illustrated in reaction example 2, N-alkyl-hydroxy/propane-diol substituted polymers may be prepared by the reaction of polyethylenimine (PEI) and an epoxide such as 2,3-epoxy-1-propanol (glycidol) in dimethyl sulfoxide (DMSO) solvent:

REACTION EXAMPLE 2

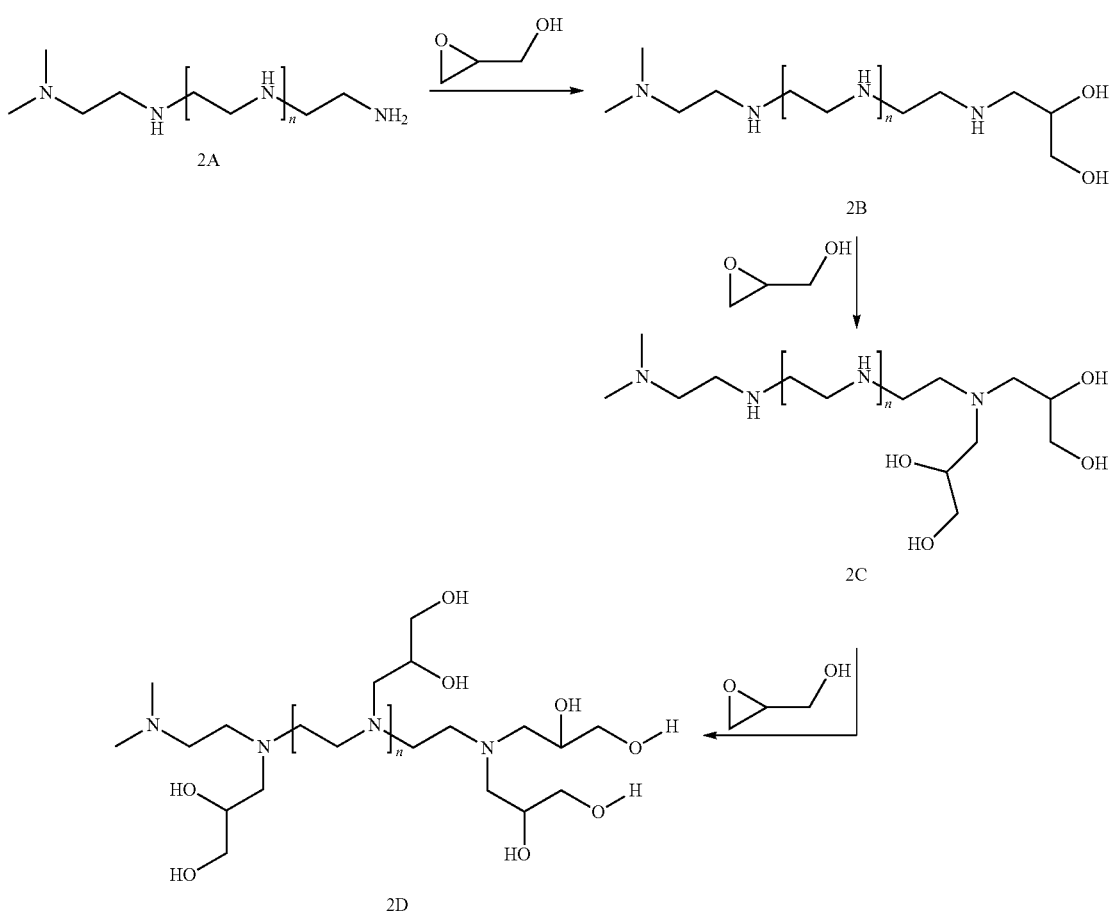

hydroxy groups have differing numbers of carbon atoms. For example, a polymer may be a mixture of N-alkyl-hydroxy groups and/or substitutions that are derived from different N-alkyl-hydroxy group precursors, such as paraformaldehyde and 2,3-epoxy-1-propanol (glycidol). In one example, a polymer of the therapeutic composition may contain 25% by mole hemiaminal groups derived from paraformaldehyde and 35% by mole of N-alkyl-hydroxy groups produced from an epoxide such as glycidol, thereby producing a composition comprising a polymer with both hemiaminal groups (one carbon atom per hemiaminal) and propane-diol groups (three carbon atoms per propane-diol group). In general, the number of combinations or different types of N-alkyl- Reaction example 2 illustrates the step-wise formation of N-alkyl-hydroxy/propane-diol substituted polymers (2B-2D) based on PEI (2A). As shown, 2A is contacted with the epoxide to produce mono-substituted N-alkyl-hydroxy/propane-diol polymer 2B (end group mono-substitution). Polymer 2C, featuring bis-N-alkyl-hydroxy/propane-diol end group substitution and thus tertiary amine end groups, is produced by additional equivalents of glycidol. Finally, 2D represents a substituted N-alkyl-hydroxy/propane-diol polymer comprising tertiary amine groups isolated upon cooling.

In one embodiment, a substituted N-alkyl-hydroxy/propane-diol polymer, such as that illustrated by 2D, may be produced by reacting and/or contacting a linear PEI of approximately 1000 g/mole with 2,3-epoxy-1-propanol (glycidol) in DMSO solvent to generate the requisite N-alkyl-hydroxy/propane-diol polymer at a temperature from about 50° C. to about 125° C., and wherein the concentration of glycidol may range from about 0.15 to about 1.5 equivalents. After isolation by precipitation in acetone or another suitable solvent, followed by washing and drying, the polymer product may be redissolved in a suitable deuterated solvent for DOSY-NMR and/or other 2D NMR techniques to analyze the polymer product and identify the peaks corresponding to the N-alkyl-hydroxy moieties. GPC may be used to determine the number average molecular weight of the substituted polymer.

N-alkyl-hydroxy substituted polymers may also be produced from carbohydrates, such as sugars, such as D-(+)-galactose. In one embodiment, as illustrated in reaction example 3, an sugar substituted polymer, comprising N-alkyl-hydroxy groups containing 6 carbon atoms and 6 hydroxy groups, may be prepared by reaction of branched PEI and D-(+)-galactose in water solvent:

REACTION EXAMPLE 3 token, some sugars may require dissolution in water or other suitable solvents at elevated temperatures for dissolution.

Generally, a polyamine, such as a branched or linear PEI, comprising a number average molecular weight from about 5,000 Da to about 20,000 Da, may be reacted with a sugar to produce N-alkyl-hydroxy substituted polymers. The mole ratio of the PEI repeat unit to the sugar is not restricted, and may range from about 1 PEI to about 0.05 sugar, such as about 1 PEI to about 0.25 sugar. Sugars suitable for production of N-alkyl-hydroxy substituted polymers include, but are not restricted to: monosaccharides (ex. triose, tetrose, pentose, and hexose), disaccharides, oligosaccharides, and polysaccharides. The sugars may be cyclic or linear, and may be structural and optical isomers. In one embodiment, a mixture of sugars, such as glucose and fructose, may be used to produce a polymer substituted with a mixture of different sugar moieties. Once produced, sugar substituted PEIs may be isolated and/or purified by any number of techniques, such as precipitation in a suitable solvent, followed by washing and drying. The polymer product may be redissolved in a suitable deuterated solvent for nuclear magnetic resonance experiments, such as DOSY-NMR and/

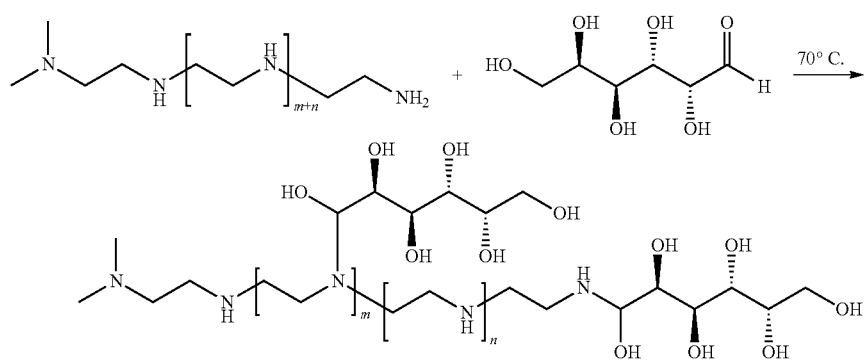

As illustrated in reaction example 3, the branched PEI comprising sugar moieties may be produced as follows: D-(+)-galactose (0.209 g, 1.163 mmol), dissolved in 2 mL of de-ionized (DI) water, may be added drop-wise to a stirred solution comprising 0.1 g (0.01 mmol) of branched PEI in 1 mL of DI water. The number average molecular weight ($M_n$), of such a PEI may be from about 5,000 Daltons (Da) to about 20,000 Da, such as 10,000 Da. The reaction solution may be further heated to a temperature from about 50° C. to about 150° C., such as 70° C., for a time period from about 4 hours to about 24 hours. Upon cooling, the solution may be freeze-dried, and may yield a dark red sticky solid material. The mole ratio for such a reaction may be 1 PEI repeat unit (—$CH_2CH_2NH$—) to 0.5 D-(+)-galactose. In other embodiments, the monosaccharide, D-(−)-arabinose, may be reacted with a linear or branched PEI, or both, using the aforementioned method to produce a sugar substituted PEI. In a further embodiment, a sugar substituted linear PEI may be produced as follows: a linear PEI ($M_n$=10,950 Da) may be dissolved in DI water at a water temperature of about 70° C., followed by drop-wise addition of D-(+)-galactose. The solution may be heated for a time period from about 12 hours to about 24 hours, to produce an N-alkyl-hydroxy substituted polymer. Importantly, because linear PEI and/or other polyamines may be insoluble in water at room temperature ($\approx$23° C.), it may be necessary to dissolve a linear PEI in warm water prior to sugar addition. By the same or other 2D NMR techniques to analyze the polymer product and identify the peaks corresponding to the N-alkyl-hydroxy moieties. Gel permeation chromatography (GPC) may also be used to determine the number average molecular weight of the substituted polymer.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A therapeutic composition, comprising:
   at least one polymer comprising:
      alkyl-hydroxy groups,
      amine groups located at the ends of the polymer chain, the polymer chain having a number average molecular weight of from about 5,000 Da to about 20,000 Da,
      secondary amine groups integrated into the polymer chain backbone,
   wherein:
      at least 5% of the amine groups located at the ends of the polymer chain comprise N-alkyl-hydroxy groups,
      at least a portion of the amine groups located at the ends of the polymer chain are saturated with N-alkyl-hydroxy groups, wherein each N-alkyl-hydroxy group comprises 1,2-diol,
      and
      the secondary amine groups integrated into the polymer chain backbone do not include N-alkyl-hydroxy groups.

2. The therapeutic composition of claim 1, wherein the polymer chain is selected from the group consisting of: polyethylenimine, polyvinylamine, polyallylamine, polyamino acrylates, polyamino methacrylates, and copolymers and salts thereof.

3. The therapeutic composition of claim 1, wherein at least a portion of the N-alkyl-hydroxy groups contain two or more carbon atoms.

4. The therapeutic composition of claim 3, wherein at least a portion of the N-alkyl-hydroxy groups comprises an epoxide adduct.

5. The therapeutic composition of claim 3, wherein at least a portion of the N-alkyl-hydroxy groups comprises a sugar adduct.

6. The therapeutic composition of claim 1, wherein the polymer comprises N-alkyl-hydroxy groups that are virus binding groups.

7. The therapeutic composition of claim 1, wherein the polymer comprises a linear chain.

8. The therapeutic composition of claim 1, wherein the polymer chain is a copolymer.

9. A therapeutic composition, comprising:
   at least one polymer comprising:
      alkyl-hydroxy groups,
      amine groups located at the ends of the polymer chain, the polymer chain selected from the group consisting of polyethyleneimine, polyvinylamine, polyallylamine, polyamino acrylates, polyamino methacrylates, and copolymers and salts thereof, the polymer chain having a number average molecular weight of from 10,000 Da to about 20,000 Da,
      secondary amine groups integrated into the polymer chain backbone, wherein:
         at least 5% of the amine groups located at the ends of the polymer chain comprise N-alkyl-hydroxy groups,
         at least a portion of the amine groups located at the ends of the polymer chain are saturated with N-alkyl-hydroxy groups,
         at least a portion of the N-alkyl-hydroxy groups comprises a 1,2-diol, and
         the secondary amine groups integrated into the polymer chain backbone do not include N-alkyl-hydroxy groups.

10. The therapeutic composition of claim 9, wherein the polymer chain is linear.

11. The therapeutic composition of claim 9, wherein the polymer chain is a copolymer.

12. The therapeutic composition of claim 9, wherein at least a portion of the N-alkyl-hydroxy groups contain two or more carbon atoms.

13. The therapeutic composition of claim 12, wherein at least a portion of the N-alkyl-hydroxy groups comprises an epoxide adduct.

14. The therapeutic composition of claim 12, wherein at least a portion of the N-alkyl-hydroxy groups comprises a sugar adduct.

* * * * *